United States Patent [19]
Dry

[11] Patent Number: 5,803,963
[45] Date of Patent: Sep. 8, 1998

[54] SMART-FIBER-REINFORCED MATRIX COMPOSITES

[76] Inventor: Carolyn M. Dry, 1505 Park Haven Dr., Champaign, Ill. 61821

[21] Appl. No.: 555,361

[22] Filed: Nov. 8, 1995

Related U.S. Application Data

[63] Continuation-in-part of Ser. No. 189,665, Feb. 1, 1994, abandoned, which is a continuation-in-part of Ser. No. 174,751, Dec. 29, 1993, Pat. No. 5,575,841, which is a continuation of Ser. No. 540,191, Jun. 19, 1990, abandoned.

[51] Int. Cl.$^6$ ............................ C04B 14/38; C04B 14/42; C04B 16/06
[52] U.S. Cl. ........................ 106/677; 106/711; 106/724; 106/802; 106/819; 106/823; 428/320.2; 428/321.1; 428/321.5; 428/364; 428/375; 523/200; 523/214; 524/80
[58] Field of Search ...................................... 106/677, 711, 106/724, 802, 819, 805, 823; 428/320.2, 321.1, 321.5, 364, 375; 523/218, 214, 200; 524/492, 80

[56] References Cited

U.S. PATENT DOCUMENTS

| | | | |
|---|---|---|---|
| 3,179,600 | 4/1965 | Brockett | 252/188.3 |
| 3,704,264 | 11/1972 | Yamato et al. | 428/240 |
| 5,575,841 | 11/1996 | Dry | 106/711 |

FOREIGN PATENT DOCUMENTS

| | | |
|---|---|---|
| 8005-529 | 1/1983 | Japan . |
| 8013-227 | 1/1983 | Japan . |
| 8013-229 | 1/1983 | Japan . |
| 1108-262-A | 4/1989 | Japan . |
| 1113-436-A | 5/1989 | Japan . |
| 2145-383-A | 6/1990 | Japan . |

OTHER PUBLICATIONS

Dry, C.M., "Building Materials Which Evolve and Adapt Over Time", Jun. 19, 1989.
Yigo, T.L. and Frost, C.M., "Temperature–Adaptable Hollow Fibers Containing Polyethylene Glycols", Apr., 1973.
Geishauser, C.B. and Cady, P.D., "A Study of the Heat Treating Cycle for Internally Sealed Concrete Containing Montan–Paraffin Wax Beads", 1977. (no month).
Kistler, Jr., C.W. and Benton, B.P., "Internal Sealing of Concrete with Degradable Polymer Beads", Aug., 1983.

*Primary Examiner*—Michael Marcheschi
*Attorney, Agent, or Firm*—Hill, Steadman & Simpson

[57] ABSTRACT

A system is provided including smart fibers which are employed to deliver agents or components to a matrix before or during cure to affect matrix cure or shaping reactions and final cured structures. The delivered agents may be reactants or catalysts to initiate or modify curing, or other agents such as heat, steam, or a coolant, for example. The system may be used to simulate bone formation, growth, and repair.

60 Claims, 5 Drawing Sheets

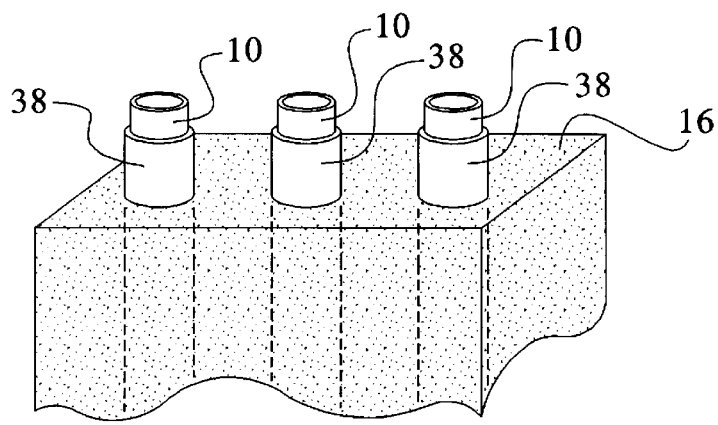
FIG.9
FIG.10a
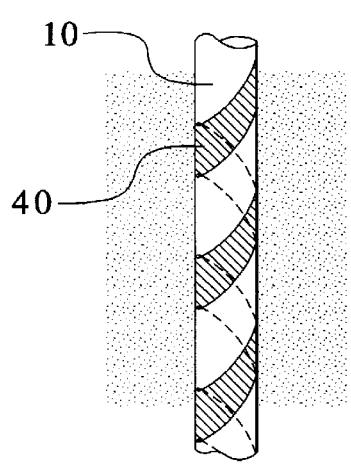
FIG.10b
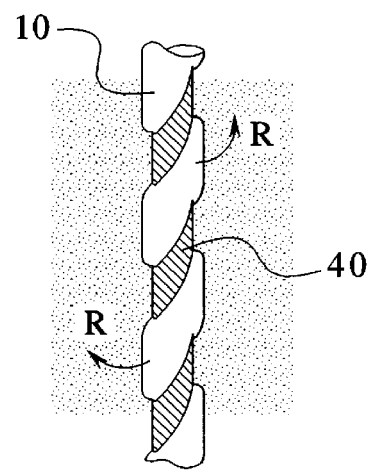
FIG.11
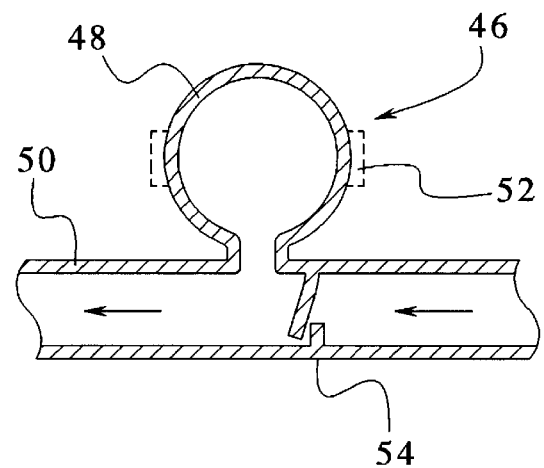

SMART-FIBER-REINFORCED MATRIX COMPOSITES

CROSS-REFERENCE TO RELATED APPLICATIONS

This application is a continuation-in-part of my prior application Ser. No. 08/189,665, filed Feb. 1, 1994, Abn which is, in turn, a continuation-in-part of U.S. Ser. No. 08/174,751, filed Dec. 29, 1993, U.S. Pat. No. 5,575,841 which is a continuation of U.S. Ser. No. 07/540,191, filed Jun. 19, 1990, now abandoned.

BACKGROUND OF THE INVENTION

The present invention generally relates to fiber-reinforced matrix materials for providing self-repairing-shaped articles and structures. More particularly, the present invention relates to new and improved fiber-reinforced matrix compositions wherein smart fibers are employed during curing and/or shaping steps to provide modified and improved curing and shaping, as well as to provide advantageous structural modifications in the final cured and shaped products. An embodiment of the present invention particularly relates to simulated bone formation, growth, and repair.

My prior application, Ser. No. 07/540,191, filed Jun. 19, 1990, Abn described the use of smart fibers, i.e., hollow fibers releasably containing repair chemicals as reinforcements as additives in organic and inorganic matrices. As described therein, shaped articles comprising a cured or shaped matrix material having loaded, pre-filled smart fibers disposed therein are provided which respond to environmental stimuli by releasing repair chemicals where and when needed to provide improved products. By way of example, shaped articles comprising a concrete or cementitious matrix containing smart fibers can respond to freeze thaw cracking, impact cracking, stress cracking and water or salt induced corrosion by releasing repair adhesives, moisture barriers and anti-corrosive chemicals to reduce or eliminate structural damage that may be caused thereby. Accordingly, improved self-repairing building structures and roads may be provided with the smart fiber-reinforced systems.

In my prior application, Ser. No. 08/189,665, filed Feb. 1, 1994, Abn new and improved smart-fiber-reinforced organic and inorganic matrix composites are described employing smart fibers alone or in combination with other specialty fibers, i.e., optical fibers, piezoelectric fibers, in various inorganic, ceramic and polymeric matrices.

My smart fiber concepts have been developed not only to provide improved self-repairing shaped articles, but also to deliver modified agents into a matrix as it is shaped and/or cured to provide enhanced or improved curing and advantageous final properties in the shaped and/or cured articles. Moreover, the smart fiber concepts may also be utilized to deliver adhesive agents in order to form a final, cured article from an array of such fibers.

As used herein, curing refers to any reactions necessary for particular matrix components to chemically combine and form a hard, structurally sound product. Chemical reactions occur during curing and/or crosslinking, generating heat and by-products. In a matrix mass, these reactions take time. Especially in large, thick matrix formations, or in certain materials, curing time can be inconveniently long. Cracking or deformation problems can arise from nonuniform temperatures through a formation during curing or from curing too fast. Moreover, a composite formation may not cure at all if it is too cool. It is, therefore, desirable to modify or enhance that curing time by influencing the reactions.

Furthermore, previous materials have displayed certain problems which result from a lack of bonding between an array of fibers and a surrounding matrix, for example, a matrix cured independently around fibers. For example, cement has little tensile strength, and a cementitious matrix has little tensile strength as well where fibers are not anchored within the matrix. In fact, fibers can weaken the matrix structure in some such materials. Therefore, it is desirable to employ a smart fiber delivery system which structurally enhances a final composite material, having fibers firmly anchored and/or chemically bonded within a surrounding matrix.

Moreover, composite materials are sometimes desirably utilized in a confined space or in an odd shape such that installation of a final composite structure would be difficult or impossible or where conventional matrix-fiber molding cannot be accomplished. In such applications, it is desirable to provide a system for forming a self-forming or self-building composite structure.

Bone formation is a particular application wherein a self-forming and self-repairing structure is needed. The natural formation of bone involves an oriented matrix secreted by osteoblasts. Bone growth occurs first through the formation of a structural organic lattice of collagen laid into a precise pattern of fibrils. Nucleation sites occur at regularly spaced intervals throughout this organic matrix. From these nucleation sites, inorganic crystalline growth moves along the organic lattice, forming a dense calcium phosphate matrix among the organic components. It is desirable to utilize hollow fiber concepts to artificially simulate the natural bone forming process.

In order to overcome the shortcomings of the previous cured or shaped materials, it is an object of the present invention to provide an improved system for initiating or enhancing a matrix curing reaction.

A further object of the present invention is to provide a system for shortening a curing time or for otherwise controlling temperature during curing, such as to prevent cracking due to nonuniform or excessively fast curing.

Still another object of the present invention is to provide a material having improved internal anchoring of fibers within a surrounding matrix, exhibiting improved anti-delamination qualities at an interface between the fibers and surrounding matrix.

Some of my prior smart fiber materials provide repair treatment modifiers to matrix locations after post-cure cracking or fracturing. While those materials are suitable for many applications, it may be desirable in some materials to modify a matrix at stressed, but unfractured, locations to prevent cracking altogether. Therefore, a further object of the present invention is to provide a new material which is self-strengthening, directing modification to stressed areas for bolstering strength before fracture.

Yet another object of the present invention is to provided a self-forming or self-building composite structure and method of making such a structure such that the structure may be formed in a confined space in which installation of a cured article or conventional molding or forming processes are not suitable.

SUMMARY OF THE INVENTION

One aspect of the present invention provides a method for making a shaped fiber-matrix composite material utilizing smart fibers to initiate or enhance curing of a final composite structure. The method includes providing a plurality of smart fibers, i.e. hollow fibers. Each hollow fiber has a pair of opposed open end portions and an intermediate portion extending between the opposed ends. The intermediate portion is preferably formed by a porous sidewall structure permitting outward release of a reactive component through the sidewall from an interior portion of the fiber. The intermediate portions of the hollow fibers are surrounded with a shapeable curable matrix composition. A reactive component is introduced into the interior portion of at least one of the hollow fibers. The reactive component is released from the intermediate portion of the hollow fiber into the curable matrix composition. The matrix composition and reactive component cure together, forming a shaped fiber matrix composite material.

In an embodiment of the invention, the reactive component is a curable composition which reacts after release to cure within the matrix composition. The matrix composition includes a co-reactive component which reacts directly with the reactive component upon release of the reactive component. According to a further aspect of the invention, another co-reactive component can be delivered or provided in the matrix which further reacts with by-products of a cure reaction of the reactive component.

For example, in an embodiment, the matrix includes cement having a monomer co-reactant which reacts with the fiber-delivered reactant to form a polymer. A by-product of this polymerization may be water which, in turn, hydrates the cement to initiate its curing. In various embodiments wherein the curable matrix composition has at least one curable monomer, the reactive component may be a reactive comonomer, crosslinking agent, hardening agent, crosslinking catalyst, or a mixture of any of these which is capable of affecting the rate or participating in a cure reaction of each curable monomer. The curable matrix composition may include either an organic or inorganic material, or a mixture of both. In some applications, the reactive component may be coated on the outside of the fiber.

In a related embodiment, the polymer and cement are selected to chemically bond into a matrix composite having optimal strength and flexibility, the materials being selected to cooperatively exhibit the best characteristics of both materials.

The hollow fibers may be provided in any number of arrangements suitable to the required delivery by the fibers and the desired final structural characteristics of the finished product. For instance, the hollow fibers may be arranged: in a parallel, spaced apart array; in bundles of grouped parallel fibers; in the form of a web; or in the form of a woven mat, etc.

An aspect of the present invention further includes the use of smart fibers to influence curing through thermal means. Such a system is particularly suitable for affecting curing of thick material sections more quickly or in any curing matrix formation wherein thermal control is desired, such as to prevent cracking from thermal stress due to nonuniform or excessively fast curing. Other composition reactive agents can be actuated by heat. To this end, a method for making an article includes providing a plurality of hollow fibers surrounded with a shapeable curable matrix composition. Each hollow fiber including a pair of opposed open end portions and an intermediate portion extending between the opposed ends. A temperature-enhancing fluid, such as a coolant, steam or other heating fluid, is introduced or flowed into the interior portion of at least one of the hollow fibers. Heat is thereby transmitted or absorbed from the intermediate portion of the hollow fiber into the curable matrix composition to either initiate or influence time of curing of the matrix composition and reactive component into a shaped fiber matrix composite material.

Another aspect of the present invention provides a system for forming "phantom" hollow fibers or channels within a matrix as it cures. To this end, smooth rods are positioned within a matrix composition before or during curing to substantial hardness. Upon setting of the matrix, the rods are then removed, leaving the hollow channels to the interior of the matrix structure. These channels can be Used to deliver repair chemicals, secondary reaction initiators, thermal fluid, etc.

According to a further aspect of the invention, hollow fibers or channels may be used to deliver a solvent or other chemical within a cured matrix to initiate a destructive reaction. The matrix structure thereby decomposes, and may be easily removed or disassembled.

Therefore, an advantage of the present invention is to provide an improved fiber-matrix composite material.

Another advantage of the present invention is to provide a system for delivering a matrix curing catalyst chemical through smart fibers.

A further advantage of the present invention is to provide a system for allowing quicker curing of thick-section composite and to reduce thermal stress during curing.

Yet another advantage is to provide means for forming composite structures without the use of conventional molding techniques. Accordingly, the present invention advantageously provides a self-forming matrix system which may be used, for example, to duplicate bone growth and repair.

Still another advantage of the present invention is to improve previously-brittle cement materials by providing ductile fibers bonded in the matrix with an inherent polymer/cement bond, resulting in a composite having superior strength properties.

A further advantage of the present invention is that the morphology and controlled reaction between phases in the matrix imparts superior properties.

Also, the present invention may be used to advantageously form a composite material under the actual stress environment and which will therefor perform in a superior manner.

A still further advantage of the present invention is to provide an improved material which is self-repairing.

Additional features and advantages of the present invention will be apparent from the Detailed Description of the Presently Preferred Embodiments and from the Figures.

BRIEF DESCRIPTION OF THE DRAWINGS

FIG. 9 is a fragmentary perspective view of fibers disposed in an uncured matrix composition, the fibers being coated by a monomer co-reactant.

FIGS. 10a–10b are fragmentary elevational views of a fiber having a constrictive member wound thereon, with FIG. 10a illustrating a normal mode and FIG. 10b illustrating a constricted mode.

FIG. 11 is a fragmentary elevated sectional view of a fiber having a pump.

DETAILED DESCRIPTION OF THE PRESENTLY PREFERRED EMBODIMENTS

Figure 1:
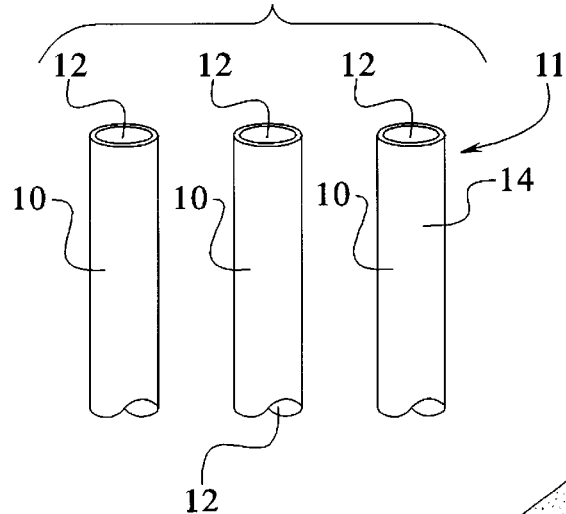
FIG. 1 is a fragmentary perspective view of a fiber array.

The present invention utilizes smart fibers to affect or modify curing of a matrix composition around the fibers, forming improved fiber-matrix composite materials. In accordance with the invention, new fiber-matrix composite materials and methods of making fiber-matrix composite structures are provided. These composite materials comprise an array of fibers surrounded by a matrix composition capable of being hardened around the fibers during curing or shaping.

Matrix materials can include any curable, settable materials such as those used in construction, building, roofing, roadway, aircraft, automotive, marine, appliances, transportation and/or biomedical fields for making shaped articles. Typically, these materials will be moldable or castable to form shaped objects or may be laminated or may be laminated or assembled into finished products. The matrix materials may be inorganic or organic in nature and may include by way of illustration: cement, concrete, phosphate cements, sintered fly ash or bottom ash/phosphoric acid mixtures, asphalt, thermoplastic polymers, thermosetting polymers, thermoplastic elastomers and hydroxylapatite. Many cementitious compounds are curable by hydration with water. Illustrative thermoplastic polymers include polyolefins, polyesters, polycarbonates, polyacrylates, polyamides, polyimides, polyaramides, polyurethanes, foaming polyurethane compositions and any other thermoplastic polymers, including room-temperature setting polymers, used as engineering thermoplastics for making shaped articles. Thermosetting polymers may include, for example, one and two part epoxies, phenolformaldehyde resins and other thermosetting polymers. Thermoplastic elastomers can include rubbery polymers and copolymers including, for example without limitation, styrenebutadiene rubber (SBR), neoprene, EPDM and silicone rubbers and the like. The matrix materials may also comprise sinterable ceramic materials including hydroxylapatites, as well as, other ceramic materials.

The matrix materials in accordance with some aspects of the present invention are processable to form shaped articles by conventional means, such as by molding, casting or thermoforming. However, the invention also permits new methods of forming shaped final structures which do not employ these conventional forming methods.

The matrix materials may be cured by means of catalysts, crosslinkers, radiation, heat, laser beam or by any means used with monomers reacting with resins or polymers in the art for setting up, hardening, rigidifying, curing or setting these matrix materials to form shaped articles or objects. The present invention provides new means for delivering various curing initiators and catalysts through hollow fibers to form the final composite structures. Also, the present invention also provides the delivery of heat or coolant through such fibers during curing to initiate or modify the curing reaction.

The hollow fiber materials may include inorganic fibers or organic fibers. Illustrative inorganic fibers include, without limitation: fiberglass fibers, cement fibers, asphalt fibers, metal fibers, and the like. Illustrative organic fibers may include polyolefin fibers, polyester fibers, polyamide fibers, polyaramid fibers, cellulose fibers, nitrocellulose fibers, Goretex® fibers, Kevlar® fibers, and the like. Porous fibers are preferably used for catalyst delivery applications, as will be described below. Nonporous fibers may be used for certain heating or cooling fiber applications.

Cementitious or ceramic composites made according to the present invention may be used for building roads, bridges, prostheses such as bone replacement or repair components, and many other applications. Polymer-based composites made according to the present invention have advantages over steel or concrete including good durability, vibration damping, energy absorption, relatively light weight and higher strength. Such polymer composite materials may be used as rebars, tensioning cables, in bonded sheets, wraps, decks, supports, beams or as the primary structures for bridges, decks or buildings. Structures made from polymer matrix materials are specially effective in aggressive environments and some embodiments are well adapted for building structures where electromagnetic transparency may be needed for highways, radar installations and hospitals.

One aspect of the present invention provides a method for making a shaped fiber-matrix composite material utilizing smart fibers to initiate or enhance curing of a final composite structure. The method includes providing a plurality of smart fibers, i.e. hollow fibers. Each hollow fiber has a pair of opposed open end portions and an intermediate portion extending between the opposed ends. The intermediate portion is preferably formed by a porous sidewall structure permitting outward release of a reactive component through the sidewall from an interior portion of the fiber. The intermediate portions of the hollow fibers are surrounded with a shapeable curable matrix composition. A reactive component is introduced into the interior portion of at least one of the hollow fibers by pumping, or the reactive component can be pre-filled within the fibers. The reactive component is released from the intermediate portion of the hollow fiber into the curable matrix composition. The matrix composition and reactive component cure together, forming a shaped fiber matrix composite material.

Referring now to FIGS. 1–4, the formation of a fiber-matrix material is illustrated in accordance with the present invention. As shown in FIG. 1, a plurality of hollow fibers 10 are provided in an array 11. Each of the illustrated hollow fibers 10 is an elongated member, having opposed open ends 12 and an intermediate sidewall portion 14 extending between the ends 12. In this embodiment, the sidewall structure is porous in order to permit permeation and the outward release of a reactive component.

Figure 2:
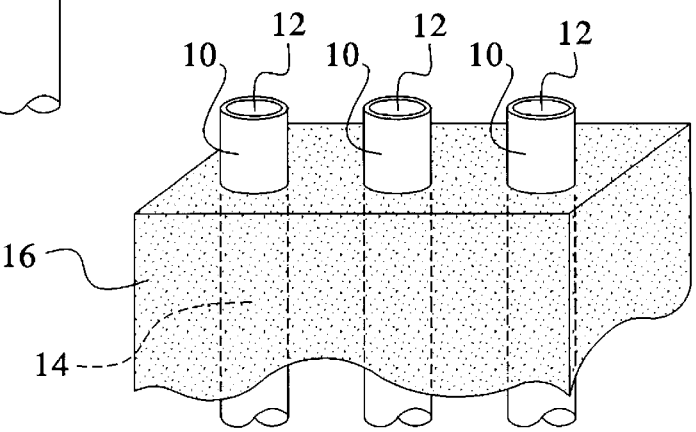
FIG. 2 is a fragmentary perspective view of the fiber array of FIG. 1 surrounded by an uncured matrix composition.

As illustrated in FIG. 2, the fibers 10 are surrounded by a curable matrix composition 16. In an embodiment, the uncured matrix composition is a powdered or viscous composition placed among the fibers. Instead, as discussed below, the matrix composition may be a coating around the fibers, such as powdered coating.

Figure 3:
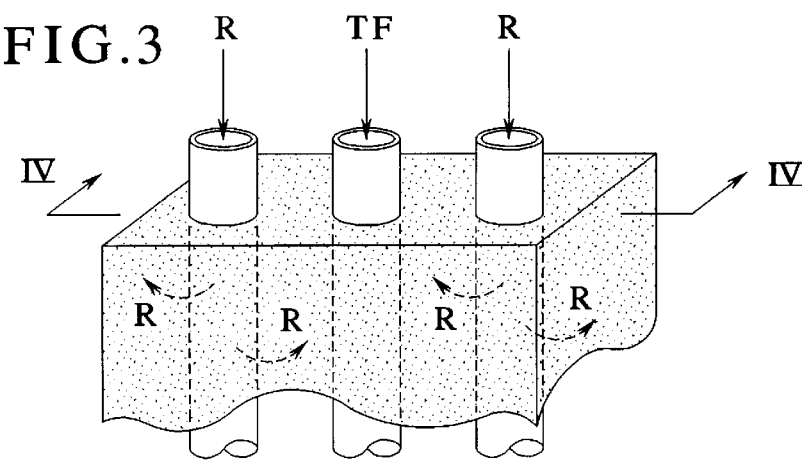
FIG. 3 is a fragmentary perspective view of the fibers and matrix composition of FIG. 2 illustrating a reactant and thermal fluid being delivered through the fibers to the matrix.

Turning to FIG. 3, a fluid reactive component R is introduced into the interior portion some or all the hollow fibers, as indicated by the arrow R. As the reactive component flows through the fiber interior, some of the reactive component is released from the pores of the intermediate portion of the hollow fiber into the curable matrix composition 16, initiating a curing reaction.

Figure 4:
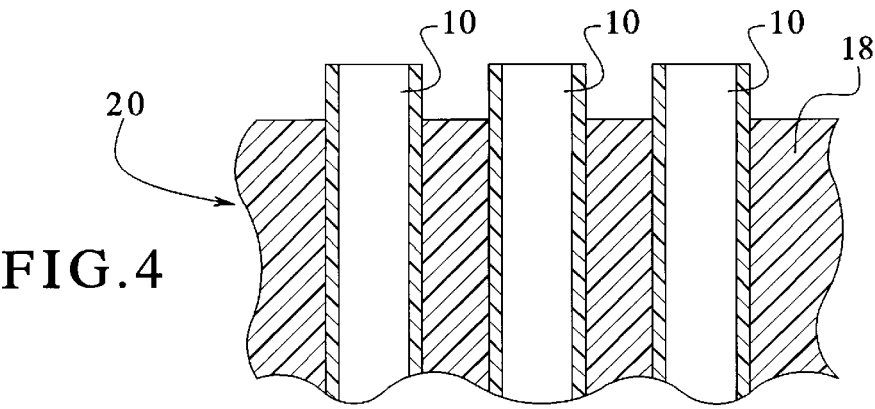
FIG. 4 is an elevated fragmentary sectional view taken generally along the line IV—IV of FIG. 3 through a cured fiber matrix composite material.

The matrix composition 16 and reactive component R subsequently cure into a cured matrix composition 18 around the fibers, as illustrated in FIG. 4, forming a shaped fiber matrix composite material 20.

In an embodiment of the invention, the reactive component R is a curable composition which reacts after release to cure within the matrix composition 16. The matrix composition includes a co-reactive component which reacts directly with the reactive component upon release of the reactive component to form the cured matrix composition 18.

Figure 5:
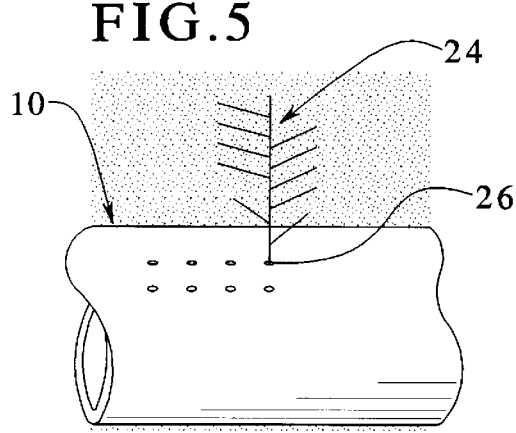
FIG. 5 is a fragmentary perspective view of a fiber having a polymer formation grown from a pore and projecting into a surrounding matrix.
Figure 6:
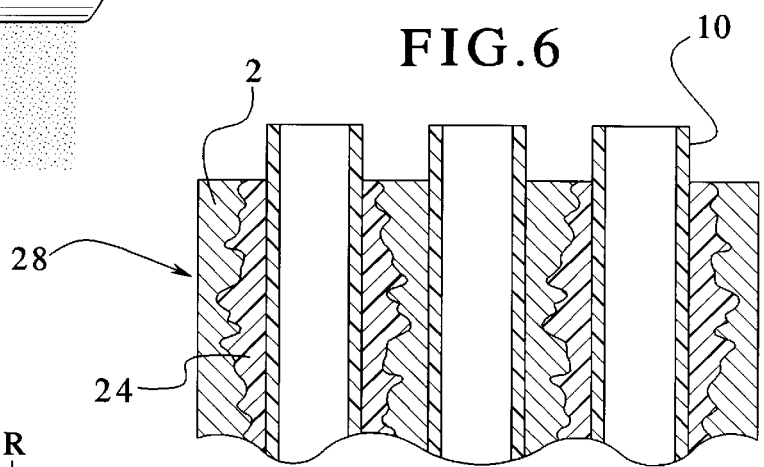
FIG. 6 is a fragmentary elevated sectional view similar to the view of FIG. 4, wherein the matrix composition has a polymer phase adjacent the reactant-delivery fibers, anchoring them to another matrix phase.

According to a further aspect of the invention, another co-reactive component can be delivered or provided in the matrix which further reacts with by-products of a cure reaction of the reactive component. For example, the heat of the initial curing reaction can activate a heat-activatable component to cause a secondary reaction. In another example, as shown in FIGS. 5 and 6, a curable matrix composition 22 includes cement having a monomer co-reactant which reacts with the fiber-delivered reactant R to form a polymer. A by-product of this polymerization may be water which, in turn, hydrates the cement or ceramic to initiate its curing. In various embodiments wherein the curable matrix composition contains at least one curable monomer, the reactive component may be a reactive comonomer, crosslinking agent, hardening agent, crosslinking catalyst, or a mixture of any of these which is capable of affecting the rate or participating in a cure reaction of each curable monomer. The curable matrix composition may include either an organic or inorganic material, or a mixture of both.

Illustrating this ceramic/polymer matrix curing process, FIG. 5 shows a polymer formation 29 projecting past each pore 26 where the reactive component R is released into the matrix composition 22, causing growth of the polymer formation 24 into the matrix composition 22. After curing, these formations 24 secure the respective pores 26 to the hardened matrix composition, resulting in a firm anchoring of the fibers 10 into the matrix. FIG. 6 illustrates a cured fiber matrix composition 28 of this type. Adjacent to selected fibers 10 used for delivery of the reactant R, the polymer formations 24 are formed, preferably having a somewhat irregular shape for good anchoring. The hydrated cementitious or ceramic/polymer matrix 30 is cured next to the polymer formation 24. The resulting fiber-matrix composite material 28 exhibits excellent antidelamination properties and has high tensile and compressive strength due to the improved anchoring of fiber in the matrix.

In a preferred embodiment, the polymer and cementitious or ceramic materials are selected for optimal compatibility to chemically bond into a matrix composite having desired strength and flexibility characteristics, exhibiting the best characteristics of both materials.

Figure 7:
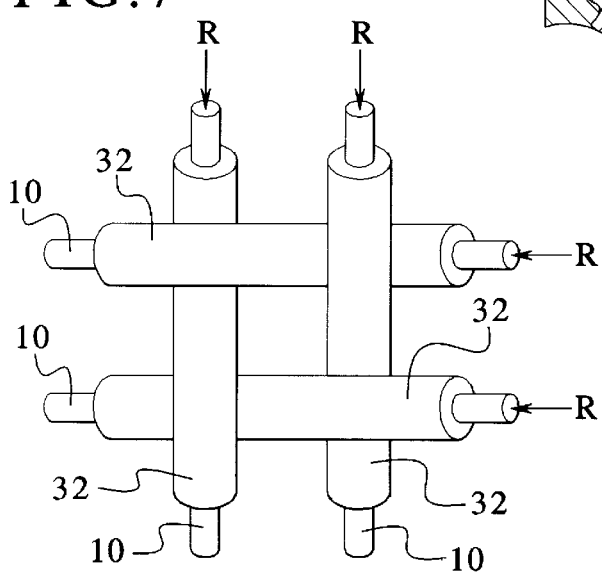
FIG. 7 is a fragmentary plan view of a web or weave of fibers coated with an uncured matrix composition, showing a reactant delivered through the fibers.
Figure 8:
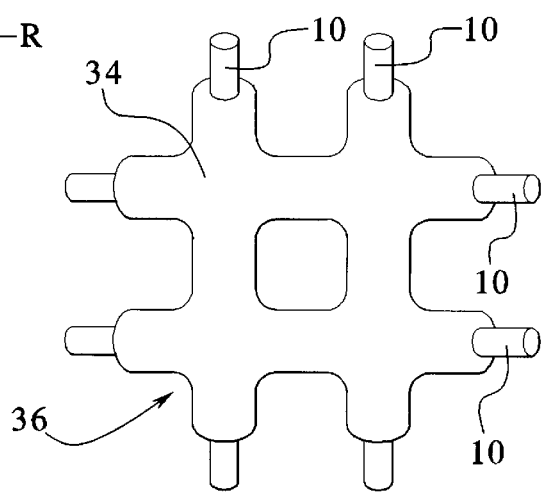
FIG. 8 is a fragmentary plan view of the fiber-matrix arrangement of FIG. 7 upon curing of the matrix composition around the fibers.

It should be understood that the matrix composition may be in any suitable form. As mentioned above, and as illustrated in FIG. 7, the curable matrix composition may be provided as a powdered coating 32 around the fibers 10. The reactant R delivered through the porous fibers 10 initiates a cure reaction with the coating 32. Neighboring and intersecting fibers 10 bond together via the resulting cured matrix material 34 into a fiber-matrix composite structure 36, as shown in FIG. 8. Still further, as illustrated in FIG. 9, the fibers 10 may have a coating 38 of the monomer co-reactant, and monomer-coated fibers 10 are surrounded by the matrix composition 16 (as a powder, second coating, etc.). The monomer coating 38 polymerizes with the supplied reactant material R from the fiber 10, forming a cured fiber-matrix composite as in FIG. 6. The coating 38 may also be actuated by laser heat to liquify and crosslink with a monomer already in the matrix. Of course, this crosslinking anchors the fibers within the matrix with good antidelamination characteristics, giving the resulting composite improved strength.

In a specialized application, a self-forming system artificially simulates natural bone formation and growth. Accordingly, an array of porous-walled hollow fibers is first provided to act as a scaffolding for matrix growth, in the same fashion as the organic collagen scaffolding first generated during natural bone growth. Matrix forming components are then delivered through the porous walled fibers, forming a linked organic/inorganic matrix which migrates along the fibers. Preferably, the delivered chemical is a liquid monomer which gives off water during crosslinking, in turn hydrating a surrounding cementitious calcium phosphate matrix component, in the manner described above. The hollow fibers concentrate the polymer and bone-like matrix component near the fiber surfaces. Ongoing self-healing may be accomplished by subsequently delivering repair chemicals through void or purged fibers to a damage site.

During a curing process, the release of the reactive component through the porous fiber wall can be assisted by squeezing the fiber 10. As illustrated in FIGS. 10a and 10b, this can be accomplished internally to the matrix by use of a squeezing member 40 which is activatable by an external stimulus. The squeezing member 40 may be made of a shape-memory alloy or a piezoelectric material. As illustrated, the squeezing member 40 is in the form of a tape which is spirally-wound around the exterior of a fiber 10. The member may be another shape, as well, such as a ring (not shown). In a normal, inactivated state, as in FIG. 10a, the member 40 performs no squeezing of the fiber 10. When activated, however, the member 40 constricts, as shown in FIG. 10b, squeezing radially inwardly on the fiber to force the reactive agent through the pores, as indicated by the arrows R. The member 22 may be made of a variety of shape-memory materials, including electroconstrictive materials actuated to constrict by an electric field stimulus, or a magnetoconstrictive material actuated to construct by a magnetic field stimulus. Upon deactivation of the stimulus, the member 22 returns to its original shape. Similarly, in an embodiment wherein the member 22 is made of piezoelectric material, the stimulus is the application of a voltage through the member 22.

In an embodiment, the fiber itself is made of a piezoelectric or shape-memory material. The piezoelectric or shape-memory fiber may be hollow with porous walls for delivering a reactant. The fiber can then be actuated with a suitable stimulus, causing the fiber walls to move, forcing the reactant from the hollow fiber into the matrix.

Also, in an embodiment, a hydrogel coating is provided around one or more fibers. The hydrogel coating is a cellulose-type layer which shrinks in the presence of water, such as water from condensation or polymerization. When wet, the hydrogel layer squeezes the associated fiber, forcing the release of initiator or other chemical from the fiber.

Shape-memory or piezoelectric material may also be used to form a pump 46 operable with one or more of the fibers. As illustrated in FIG. 11, the pump 46 may include a bulb 48 extending from a fiber 50. The bulb 48 has an interior in communication with the fiber interior. The pump 46 may be made of shape memory alloy or piezoelectric material. Optionally, the bulb 48 may be made of the same material as the fiber and have a squeezing element 52 disposed around the bulb 48 made of shape-memory alloy or piezoelectric material. Actuation of the shape-memory alloy or piezoelectric material causes the bulb 48 to shrink or be squeezed, evacuating the bulb interior into the fiber 50. A valve 54 keeps the flow in a desired direction, as indicated by the arrows. Deactuation of the shape-memory alloy or piezoelectric material causes the bulb 48 to relax, drawing in fluid. Repeated actuation and deactuation results in a pumping of fluid through the hollow fiber 50.

Figure 12:
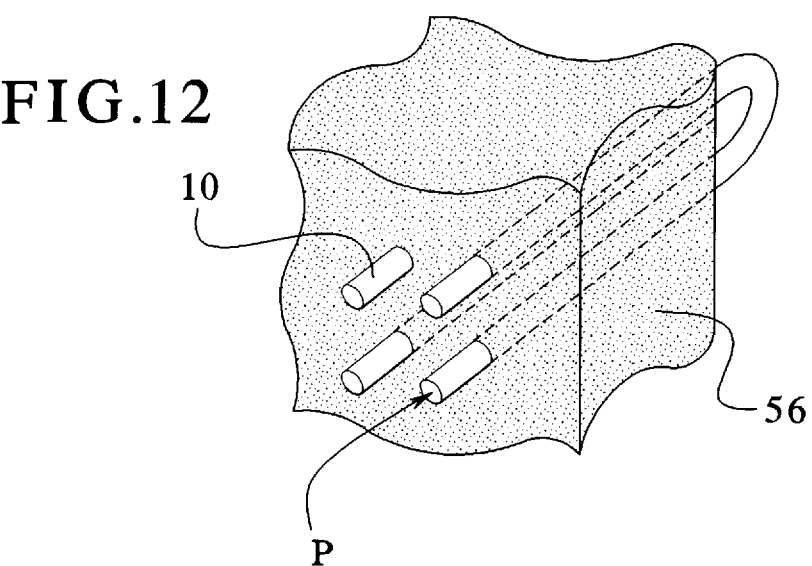
FIG. 12 is a fragmentary perspective view of fibers in a matrix being purged.

Re-use of the delivery fibers is possible so long as the delivered fluid is purged from the hollow fiber interior after an appropriate amount has been delivered. For example, the fibers 10 within a cured or curing matrix 56 may be purged by air pressure, as indicated in FIG. 12 by the arrow P, forcing the fluid from the fibers 10. Also, squeezing the fibers 10 by a squeezing member 40, as described in connection with FIGS. 10a and 10b, or by a pump 46, as described in connection with FIG. 11 can assist in purging, preferably if performed prior to hardening of the matrix in order to avoid delamination of the fiber wall from the matrix. Once a fiber interior has been cleared, that same fiber 10 can be used to deliver a thermal fluid, a modifier or repair chemical to subsequently modify the composite material.

Post-cure delivery through the fibers can affect repair of damaged matrix locations, temperature, or initiate a subsequent reaction. Furthermore, purged or void fibers or channels may be used to deliver a solvent or other chemical within a cured matrix to degrade the matrix. The matrix structure thereby self-destructs by weakening or disintegration for removal or disassembly.

Figure 13:
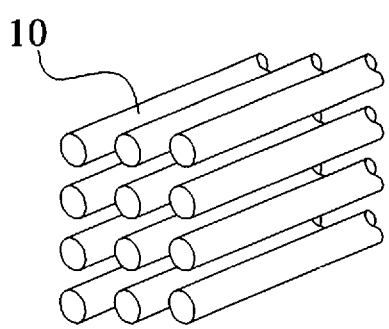
FIG. 13 is a fragmentary perspective view of fibers disposed in a parallel, spaced array.
Figure 14:
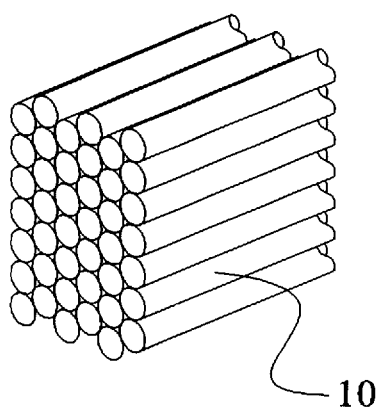
FIG. 14 is a fragmentary perspective view of an array of fibers disposed in a bundle.
Figure 15:
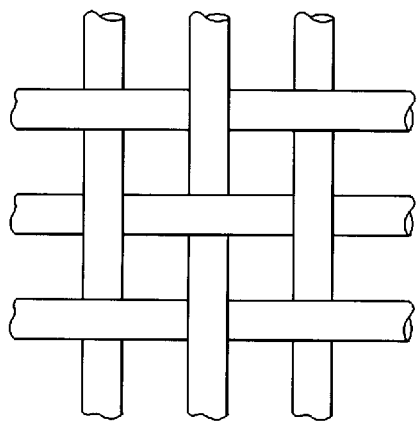
FIG. 15 is a plan view of an array of fibers arranged in a weave or web.

The hollow fibers may be provided in a variety of arrangements suitable for a particular application with the matrix. A selected arrangement may depend on the required delivery locations within the matrix. Also, the fibers may be prearranged in the general net shape of the desired final composite structure. Such a prearranged near-net shape can be used to avoid some conventional formation process such as molding. Moreover, the fiber arrangement may be selected to provide desired reinforcing structural characteristics within the final, cured product. For example, without limitation, the hollow fibers 10 may be arranged in a parallel, spaced apart array, as illustrated in FIG. 13, in bundles of grouped parallel fibers 10, as illustrated in FIG. 14, or in the form of a woven web or mat, as illustrated in FIG. 15. The array of fibers may also be a random arrangement within the matrix.

Figure 16:
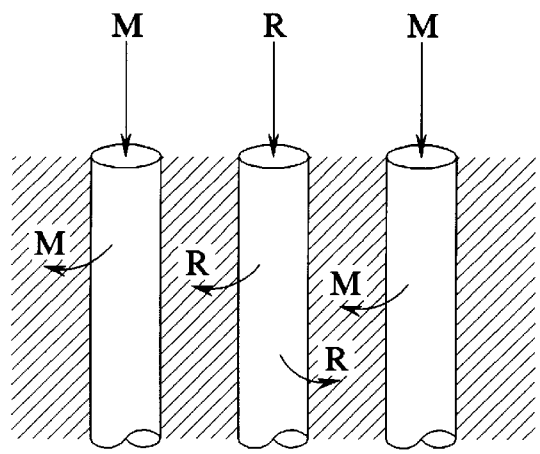
FIG. 16 is a schematic perspective view of a fiber matrix composite which shows fibers delivering a two-part adhesive matrix.
Figure 17:
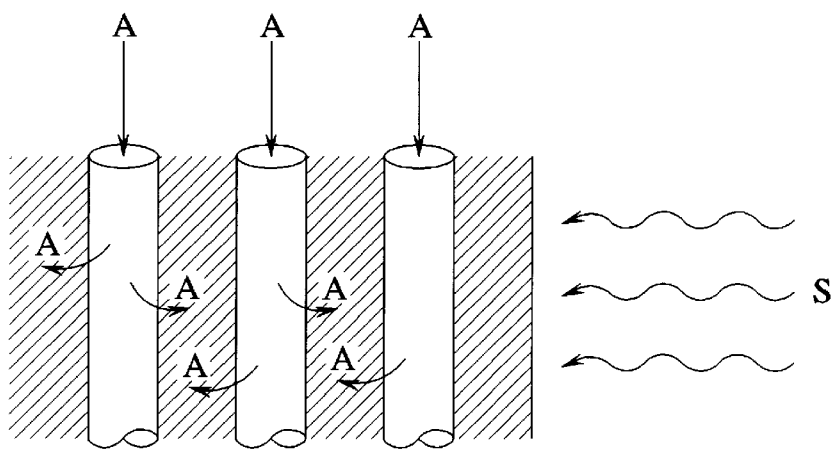
FIG. 17 is a schematic perspective view of a fiber matrix composite which shows fibers delivering a one-part adhesive matrix activated by an external stimulus.

Turning now to FIGS. 16 and 17, hollow fibers can be used to deliver all matrix materials through the fibers, including all matrix components, initiators, latent initiators or modifiers, etc., instead of pre-surrounding the fibers with a matrix component such as a powder. More specifically, the fibers can either supply a one-part adhesive matrix component or separate fibers can supply separate matrix and reactant components M and R, respectively, as illustrated in FIG. 16, which combine to form the matrix. These processes are especially useful for creating a self-forming structure through an array of fibers generally shaped as a desired final article.

As shown in the embodiment of FIG. 16, the matrix component M is a liquid delivered through some of the hollow fibers 10. The matrix component M permeates through the porous wall of the fibers 10 to generally surround the fibers 10 in the array. The reactive component R is provided through other fibers from which it permeates to commingle with the matrix component M. The matrix component M and reactive component R react to initiate curing of a final matrix material. For example, the two-part matrix material can be an epoxy resin and hardener.

Also, as illustrated in FIG. 6, a one-part matrix component A may be provided through some or all of the fibers 10. The one-part component A permeates through the fiber walls 10 and surrounds the array. The one-part adhesive matrix component A can be a simple adhesive such as glue, however, the one-part adhesive matrix component A preferably comprises a liquid compound, e.g., epoxy resin, containing a latent or inert catalyst component. This latent catalyst is activatable by a suitable external stimulus S. For example, the latent hardener component may be a light-activatable photoinitiator stimulated by light, a heat-activatable component activatable by a heat source such as a laser, an radiation-activatable component activated by ultraviolet, electron beam, or gamma radiation. The external stimulus breaks down the inert, latent agent into activated catalyst to initiate curing. These processes might be utilized in applications where it is desirable to avoid autoclaving. The latent catalyst or repair chemical may also be delivered through a fiber at a delaminated location or through a break in a fiber caused by a break or crack in the composite structure.

The present invention also provides for the utilization of hollow smart fibers to thermally influence a matrix, such as during curing. It is recognized that some curing reactions such as polymerization can generate a substantial amount of heat. Particularly in conventional thick-section composite formations, heat is not efficiently dissipated and can build to excessive levels. If the heat exceeds the thermal stress limits of the matrix composition, the material can be damaged by cracking and weakening. Such damage may also result by uneven curing rates within the composite formation.

The present invention solves such problems by providing a flow of thermal transfer fluid TF, as shown, for example, in FIG. 3, in order to control the curing time and/or to more uniformly cure a curing composite structure. For example, the thermal fluid TF can be a coolant supplied through at least some fibers in the matrix to dissipate excessive heat or to reduce curing time. Similarly, the thermal fluid TF can be a heated fluid supplied through all or selected fibers in order to prevent cracking due to thermal stresses from curing too quickly or in order to effect curing in an environment which would otherwise be too cool for the curing reaction to complete. Moreover, the temperature of the matrix may be controlled by heating or cooling during curing to achieve a more uniform curing rate through a composite piece, preventing distortion and cracking.

Also, a thermal transfer fluid TF supplied through the fibers may heat the matrix in order to initiate curing by a heat-activatable component in the matrix or to slow the curing rate. Moreover, such a heat transfer into the matrix may be used in post-curing applications, such as to activate a heat-activatable modifier component to repair the matrix microstructure. The heated thermal transfer fluid TF may be, for example, steam.

Figure 18:
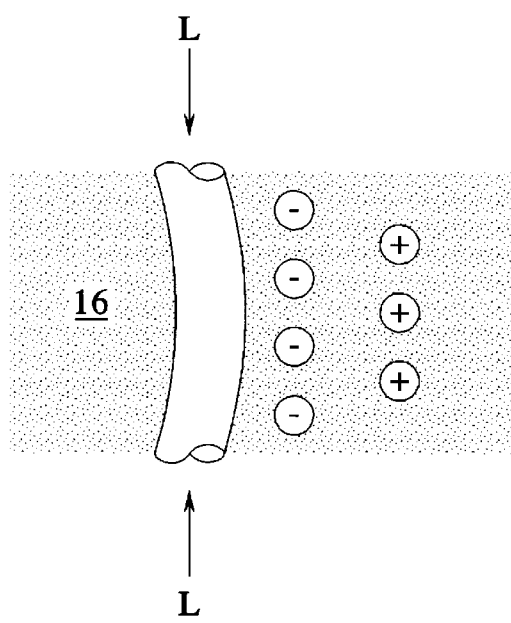
FIG. 18 is a schematic perspective view of a piezoelectric fiber under stress and causing a migration of ions in a curing matrix.

In accordance with a further aspect of the present invention, a composite material, preferably cementitious or ceramic, is provided having a structure organized to resist environmental forces. Some or all of the fibers are electrically charged to influence the arrangement of matrix ions during curing. As illustrated in FIG. 18, some or all of the fibers 10 may be made of a piezoelectric material. Preferably, the piezoelectric fibers are hollow so that they can be used for delivering a reactant during curing, in the manner as described above, however, one or more of the piezoelectric fibers may be solid. A prestress on the piezoelectric fiber, as indicated by a load L, generates a charge on the fiber surface, as indicated in FIG. 11. The load L could be in another direction than illustrated. From the charged fiber location, a migration of ions takes place through the matrix material, such as cement ions through a cement matrix, bolstering the strength or altering the characteristics of the composite material at the stressed location. For example, a prestress on one of the piezoelectric fibers, such as an environmental load on the fiber framework, may cause a negative charge on the fiber's surface, as illustrated, pulling positive ions from the curing matrix composition toward the fiber. This results in zones of desired strength characteristics in the final cured structure. These zones can be created for bolstering composite strength at a particularly stressed location of the composite element.

In another embodiment, one or more of the fibers 10 is a conductor, such as metal, instead of a piezoelectric material. The metal fiber is charged by a voltage source in order to achieve a similar migration of ions through a curing composite structure. The metal fibers may be hollow and have holes located in the fiber walls to deliver initiator, repair, or thermal fluids.

The fiber-delivery processes of the present invention can be customized for special applications by fiber location and fluid-delivery timing. Fibers may be arranged within the array so that certain fibers extend to one or more specific locations within the matrix. On the other hand, fibers may be designed to extend substantially throughout the matrix for a effectively delivering within the total matrix. Moreover, separate fibers may be used to simultaneously deliver different agents within the matrix. Also, fluid delivery through selected fibers can be timed to cure various parts of the matrix at different times or to initiate a given reaction within the matrix at a selected time during a sequence of events.

It should be understood that various changes and modifications to the presently preferred embodiments will be apparent to those skilled in the art. For example, multiple applications described herein may be performed in a fiber-matrix arrangement, such as using some fibers for delivery of a reactive agent and others for thermal transfer. Other fibers may remain hollow until used for delivery of a post-cure treatment chemical. Also, it should be recognized that the present invention may be used for manufacturing composite components in a factory environment, but may also be used in the field where the necessary chemicals, initiators, modifiers, repair compounds, thermal fluids, etc., are stored for delivery through the fibers. Such changes and modifications may be made without departing from the spirit and scope of the present invention, and without diminishing its attendant advantages. Therefore, it is intended that such changes and modifications be covered by the appended claims.

I claim:

1. A method for making a shaped fiber-matrix composite material comprising the steps of:

preparing a plurality of hollow fibers, each hollow fiber including a pair of opposed open end portions and an intermediate portion extending between the opposed ends, the intermediate portion having a sidewall structure permitting outward release of a reactive component through the sidewall from an interior portion of the fiber;

surrounding the intermediate portions of the hollow fibers with a shapeable curable matrix composition;

introducing a reactive component into the interior portion of at least one of the hollow fibers;

releasing reactive component from the intermediate portion of the hollow fiber into the curable matrix composition; and curing the matrix composition and reactive component to form the shaped fiber matrix composite material.

2. The method as defined in claim 1, wherein said matrix composition further comprises a co-reactive component which reacts directly with the reactive component upon release of the reactive component.

3. The method as defined in claim 2, wherein, prior to curing, said co-reactive component is in the form of a coating around at least one of the fibers.

4. The method as defined in claim 1, wherein said reactive component includes a self-curing composition which reacts after being released to cure within the matrix composition.

5. The method as defined in claim 4, wherein the matrix composition further comprises a co-reactive component which reacts with a by-product of a cure reaction of the reactive component.

6. The method as defined in claim 5, wherein said by-product includes water.

7. The method as defined in claim 6, wherein the matrix composition is a cementitious material, said co-reactive component is a monomer, said method further comprising:

polymerizing said co-reactive component with said reactive component, wherein the water is given off as condensation from the polymerizing; and hydrating the cementitious material with the water.

8. The method as defined in claim 5, wherein said by-product includes heat.

9. The method as defined in claim 1, wherein the hollow fibers are prepared in a parallel, spaced apart array of fibers.

10. The method as defined in claim 1, wherein the hollow fibers are prepared in bundles of grouped parallel fibers.

11. The method as defined in claim 1, wherein the hollow fibers are prepared in the form of a web.

12. The method as defined in claim 1, wherein the hollow fibers are arranged in the form of a net shape.

13. The method as defined in claim 1, wherein said curable matrix composition includes at least one curable monomer and said reactive component comprises comonomers, crosslinking agents, hardening agents, crosslinking catalysts or mixtures of any of the foregoing.

14. The method as defined in claim 1, wherein said curable matrix composition comprises an organic material.

15. The method as defined in claim 1, wherein said curable matrix composition comprises an inorganic material.

16. The method as defined in claim 1, wherein said curable matrix composition comprises a mixture of inorganic and organic materials.

17. The method as defined in claim 1, wherein, prior to curing, said curable matrix composition is a powder.

18. The method as defined in claim 1, wherein, prior to curing, said curable matrix composition is a liquid.

19. The method as defined in claim 1, wherein, prior to curing, said curable matrix composition is a coating around some of the fibers.

20. The method as defined in claim 1, wherein the surrounding step includes delivering a matrix component in liquid form through at least one fiber, from which the matrix component permeates through the fiber to its exterior.

21. The method as defined in claim 1, wherein at least one of the fibers is made of piezoelectric material.

22. The method as defined in claim 21, wherein the method further comprises:

stressing the piezoelectric fiber during curing.

23. The method as defined in claim 21, wherein the method further comprises:

applying a voltage through the piezoelectric fiber during curing to cause the fiber to move.

24. The method as defined in claim 1, wherein at least one of the fibers is made of a conductive material, the method further comprising:

applying an electrical charge to the conductive fiber during curing.

25. The method as defined in claim 1, wherein the releasing step includes:

actuating at least one constrictive element which is disposed at least partially around at least one of the fibers thereby delivering said reactive component by squeezing the fiber.

26. The method as defined in claim 25, wherein the constrictive element is made of a shape memory alloy including a material selected from the group consisting of magnetoconstrictive materials and electroconstrictive materials.

27. A method as defined in claim 25, wherein the constrictive element is made of a hydrogel material which constricts in the presence of water.

28. The method according to claim 1, further comprising the step of:

providing a bulbous extension of the fiber; and squeezing the bulbous extension of the fiber to pump fluid therefrom.

29. The method according to claim 28, wherein a shape-memory material is disposed around the bulbous extension, the method further comprising:

activating the shape-memory material with a stimulus to constrict the shape-memory material around the bulbous extension.

30. The method according to claim 28, wherein the bulbous extension is made of shape-memory material, the method further comprising:

activating the shape-memory material with a stimulus to constrict the bulbous extension.

31. The method according to claim 28, wherein the bulbous extension is made of piezoelectric material, the method further comprising:

applying an electric charge to the piezoelectric material to constrict the bulbous extension.

32. The method as defined in claim 1 further comprising:

introducing a thermal transfer fluid into the interior portion of at least one of the hollow fibers; and transferring thermal energy between the intermediate portion of the hollow fiber and the matrix composition.

33. The method as defined in claim 32, wherein the thermal transfer fluid is a coolant, and whereby the transferring of thermal energy is an absorption of heat into the coolant from the matrix composition.

34. The method as defined in claim 32, wherein the thermal transfer fluid is a heated fluid, and whereby the transferring of thermal energy is absorption of heat into the matrix composition from the heated fluid.

35. The method as defined in claim 34, wherein the thermal energy activates a heat-activatable modifier.

36. The method as defined in claim 1, further comprising:

purging the reactive component from at least one of the hollow fibers so that the hollow fiber is reusable for delivery of a fluid into the matrix composition after curing.

37. The method as defined in claim 1, further comprising:

delivering a repair component through at least one of the fibers to a damaged site of the cured matrix composition.

38. The method as defined in claim 1, further comprising:

delivering a chemical through at least one of the fibers into the cured fiber matrix composition, to cause chemical degrading of the cured matrix composition.

39. A method for making a shaped fiber-matrix article comprising:

preparing a plurality of hollow fibers, each hollow fiber including a pair of opposed open end portions and an intermediate portion extending between the opposed ends;

surrounding the intermediate portions of the hollow fibers with a shapeable curable matrix composition;

initiating a curing of the matrix composition;

introducing a thermal transfer fluid into the interior portion of at least one of the hollow fibers;

transferring thermal energy between the thermal transfer fluid and the matrix composition through the intermediate portion of the hollow fiber; and curing the matrix composition to form a shaped fiber matrix composite material.

40. The method as defined in claim 39, wherein the thermal transfer fluid is a coolant, and whereby the transferring of thermal energy is an absorption of heat from the matrix composition to the coolant.

41. The method as defined in claim 39, wherein the thermal transfer fluid is a heated fluid, and whereby the transferring of thermal energy is absorption of heat into the matrix from the heated fluid.

42. The method as defined in claim 41, wherein the heated fluid is steam.

43. The method as defined in claim 41, wherein the matrix composition includes a heat activatable component, and whereby the initiating step is a result of delivering heat to the matrix.

44. The method as defined in claim 39, wherein at least one of the hollow fibers has a porous wall and wherein the initiating step includes:

delivering a reactive component to the matrix component through the porous wall of the fiber.

45. A method for making a shaped fiber-matrix composite material comprising the steps of:

preparing a plurality of hollow fibers, each hollow fiber including a pair of opposed open end portions and an intermediate portion extending between the opposed ends, the intermediate portion having a sidewall structure permitting outward release of an adhesive component through the sidewall from an interior portion of the fiber, the plurality of hollow fibers being bundled together in an array of fibers;

introducing the adhesive component into the interior portion of at least one of the hollow fibers;

releasing adhesive component from the intermediate portion of the hollow fiber between the hollow fiber and adjacent hollow fibers in the array; and curing the adhesive component in the array to form a shaped matrix-fiber composite structure.

46. The method as defined in claim 45, wherein at least one of the fibers delivers a reactive component which reacts with the adhesive component to initiate the curing step.

47. The method as defined in claim 45, wherein the adhesive component is a one-part epoxy containing a latent catalyst component which is activatable by an external stimulus to initiate the curing step.

48. The method as defined in claim 47, wherein the latent catalyst is a photoinitiator, and wherein the external stimulus is light.

49. The method as defined in claim 47, wherein the external stimulus is heat.

50. The method as defined in claim 47, wherein the external stimulus is a laser beam.

51. The method as defined in claim 47, wherein the external stimulus is actinic radiation.

52. A fiber-matrix composite material comprising:

a cured matrix material having at least one hollow fiber disposed therein, said hollow fiber having a wall with a plurality of pores, the matrix material having a plurality of polymer formations interspersed therein, such that at least some of the formations stem from pores, the formations anchoring the fibers to the matrix material.

53. A method of making a fiber-matrix composite material comprising the steps of:

preparing a curable matrix composition around one or more rods;

initiating a curing of the matrix composition;

removing the rod from the matrix composition after the matrix composition has set, forming a hollow channel in the set matrix composition;

delivering a fluid through the hollow channel.

54. The method according to claim 53, wherein the delivering occurs during curing of the matrix composition.

55. The method according to claim 53, wherein the delivering occurs after curing of the matrix composition.

56. The method according to claim 53, wherein the fluid is a coolant to cause a transfer of heat from the matrix composition to the fluid during curing.

57. The method according to claim 53, wherein the fluid transfers heat into the matrix composition.

58. The method according to claim 57, wherein the heat activates a heat-activatable component in the matrix to cause a chemical reaction.

59. The method according to claim 53, wherein the fluid is a chemical which reacts with a compound in the matrix composition.

60. The method according to claim 59, wherein the chemical is a solvent which degrades the matrix composition.

* * * * *